US010620148B2

(12) United States Patent
Marquant

(10) Patent No.: US 10,620,148 B2
(45) Date of Patent: Apr. 14, 2020

(54) METHOD AND TEST ELEMENT FOR ELECTROCHEMICALLY DETECTING AT LEAST ONE ANALYTE IN A SAMPLE OF A BODY FLUID

(71) Applicant: Roche Diagnostics Operations, Inc., Indianapolis, IN (US)

(72) Inventor: Michael Marquant, Mannheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 15/830,672

(22) Filed: Dec. 4, 2017

(65) Prior Publication Data
US 2018/0100826 A1    Apr. 12, 2018

Related U.S. Application Data

(63) Continuation of application No. PCT/EP2016/063453, filed on Jun. 13, 2016.

(30) Foreign Application Priority Data

Jun. 15, 2015    (EP) .................................... 15172083

(51) Int. Cl.
*G01N 27/30*    (2006.01)
*G01N 27/327*    (2006.01)
(Continued)

(52) U.S. Cl.
CPC ........... *G01N 27/301* (2013.01); *C12Q 1/006* (2013.01); *C12Q 1/54* (2013.01); *G01N 27/3272* (2013.01)

(58) Field of Classification Search
CPC ...... G01N 27/327–3272; G01N 27/301; A61B 5/1468; A61B 5/1486; A61B 5/14865; C25D 3/56; C25D 3/64
(Continued)

(56) References Cited

U.S. PATENT DOCUMENTS 4,795,542 A *  1/1989  Ross ................... G01N 27/3271
                                                  204/403.09
5,288,636 A *  2/1994  Pollmann ............... C12Q 1/004
                                                  204/403.14
(Continued)

FOREIGN PATENT DOCUMENTS

CN        201885997 U    6/2011
EP         1343007 A1    9/2003
(Continued)

OTHER PUBLICATIONS

Dissertation of Erik Uwe Arango Gutierrez entitled "Optimization of Glucose oxidase towards oxygen independency and high mediator activity for amperometric glucose determination in diabetes analytics" von der Fakultät für Mathematik, Informatik and Naturwissenschaften der RWTH Aachen University. (Year: 2014).*

(Continued)

*Primary Examiner* — Alexander S Noguerola
(74) *Attorney, Agent, or Firm* — Roche Diagnostics Operations, Inc.

(57) ABSTRACT

A method and test element for electrochemically detecting at least one analyte in a sample are provided, wherein the method comprises: a) providing at least one test element comprising at least one first electrode contacting a test chemistry and at least one second electrode, wherein a surface of the second electrode consists of silver metal; b) contacting both the first and second electrodes with the sample comprising chloride ions; c) applying a first voltage between the first electrode as a cathode and the second electrode as an anode with a voltage sufficient for forming a layer of silver chloride at the surface of the second electrode; d) applying a second voltage between the first electrode as the anode and the second electrode as the cathode; and e) determining an electrical signal between the (Continued)

first and the second electrodes, whereby the analyte in the sample comprising the chloride ions is detected.

13 Claims, 4 Drawing Sheets

(51) Int. Cl.
*C12Q 1/00* (2006.01)
*C12Q 1/54* (2006.01)

(58) Field of Classification Search
USPC .......................................................... 205/258
See application file for complete search history.

(56) References Cited

U.S. PATENT DOCUMENTS

| | | | | |
|---|---|---|---|---|
| 5,589,045 | A | * | 12/1996 | Hyodo .............. G01N 33/48792 204/403.11 |
| 5,682,884 | A | | 11/1997 | Hill et al. |
| 6,153,069 | A | * | 11/2000 | Pottgen .............. G01N 27/3273 204/400 |
| 6,885,196 | B2 | * | 4/2005 | Taniike .................. C12Q 1/005 204/403.11 |
| 7,258,769 | B2 | * | 8/2007 | Cui .................. B01L 3/502715 204/403.01 |
| 2002/0112969 | A1 | | 8/2002 | Hodges et al. |
| 2003/0146113 | A1 | | 8/2003 | Unkrig et al. |
| 2005/0123441 | A1 | | 6/2005 | Unkrig et al. |
| 2006/0016700 | A1 | | 1/2006 | Brister et al. |
| 2009/0294306 | A1 | | 12/2009 | Feldman et al. |
| 2009/0298104 | A1 | | 12/2009 | Liu et al. |
| 2012/0211363 | A1 | * | 8/2012 | Anorga Gomez ... G01N 27/301 204/435 |
| 2012/0267245 | A1 | | 10/2012 | Chambers et al. |
| 2017/0240945 | A1 | | 8/2017 | Marquant et al. |

FOREIGN PATENT DOCUMENTS

| | | | |
|---|---|---|---|
| JP | H06-102230 A | 4/1994 | |
| KR | 0135367 B1 | 7/1998 | |
| WO | WO 95/04272 A1 * | 2/1995 | ........... G01N 27/327 |
| WO | 1999/045375 A1 | 9/1999 | |
| WO | 2003/056345 A1 | 7/2003 | |
| WO | 2003/076648 A1 | 9/2003 | |

OTHER PUBLICATIONS

Hönes, Joachim et al., The Technology Behind Glucose Meters: Test Strips, Diabetes Technology & Therapeutics, 2008, pp. S-10-S-26, vol. 10, Supplement 1.

International Search Report dated Aug. 25, 2016, in Application No. PCT/EP2016/063453, 5 pp.

\* cited by examiner

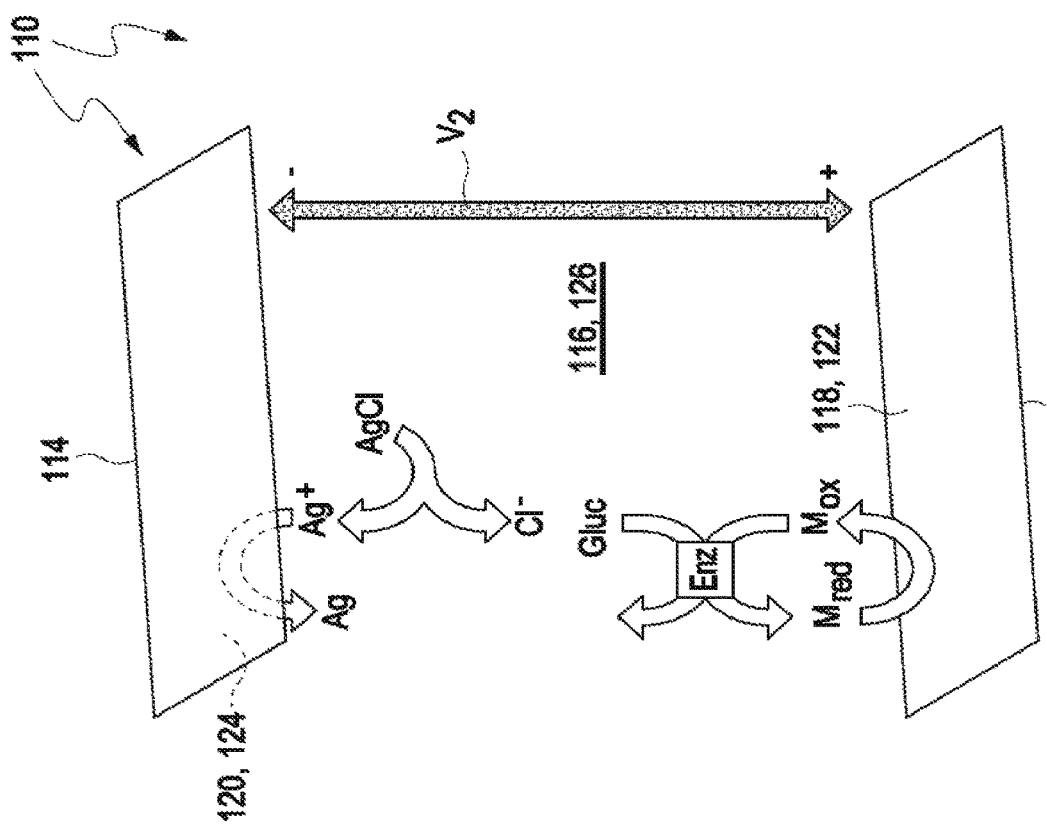
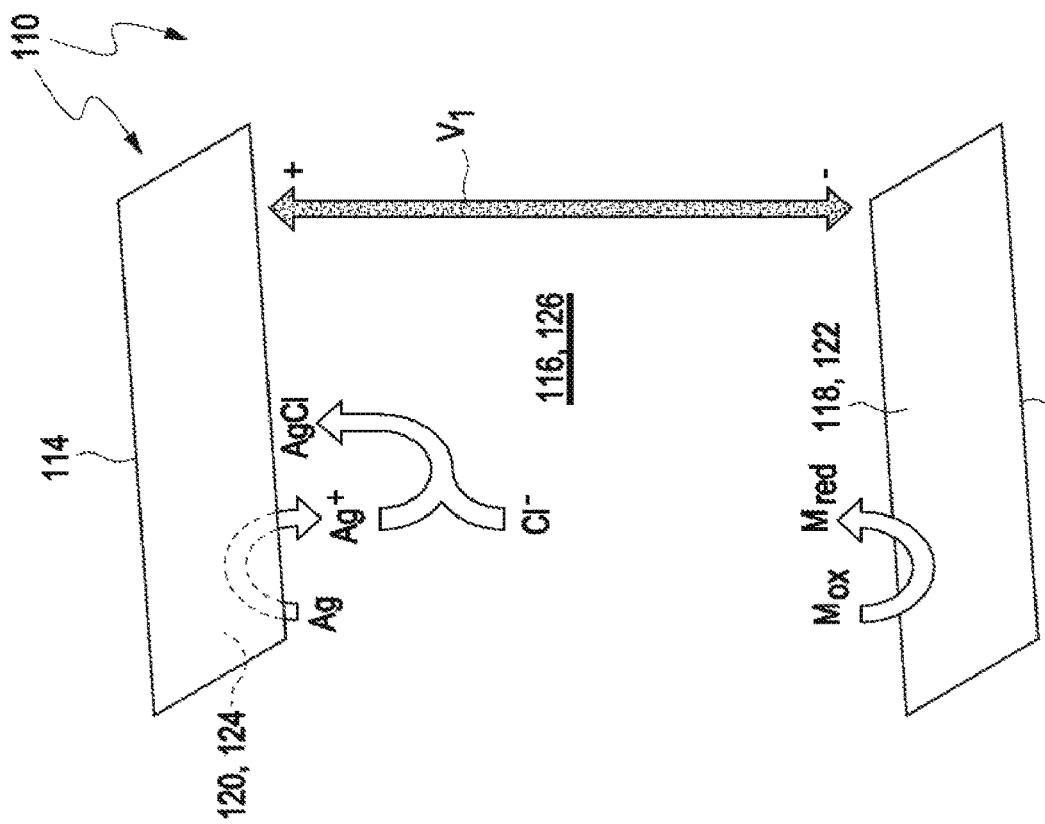

METHOD AND TEST ELEMENT FOR ELECTROCHEMICALLY DETECTING AT LEAST ONE ANALYTE IN A SAMPLE OF A BODY FLUID

CROSS-REFERENCE TO RELATED APPLICATIONS

This application is a continuation of International Application No. PCT/EP2016/063453, filed 13 Jun. 2016, which claims the benefit of European Patent Application No. 15172083.6, filed 15 Jun. 2015, the disclosures of which are hereby incorporated by reference in their entirety.

FIELD OF THE DISCLOSURE

The present disclosure relates to a method and a test element for electrochemically detecting at least one analyte in a sample of a body fluid and, in particular, a method for producing the test element, a method for generating a layer of silver chloride at a surface of an electrode of the test element, and a system for determining at least one property of the sample of the body fluid, wherein the system comprises the test element.

BACKGROUND

In the field of medical technology and diagnostics, a large number of devices and methods for detecting at least one analyte in a body fluid are known. The methods and devices may be used for detecting at least one analyte present in a body tissue or a body fluid, in particular one or more analytes such as glucose, lactate, triglycerides, cholesterol or other analytes, typically metabolites, in body fluids such as blood, typically whole blood, plasma, serum, urine, saliva, interstitial fluid or other body fluids. Further devices are known for measuring activating times, e.g., a thrombin activation time measurement for coagulation monitoring. Without restricting the scope of the present disclosure, reference is made to the detection of glucose as an exemplary and typical analyte in the following.

The determination of blood glucose concentration as well as a corresponding medication is an essential part of daily routine for many diabetics. In order to increase convenience and in order to avoid restricting the daily routine by more than a tolerable degree, portable devices and test elements are known in the art, such as for measuring blood glucose concentration during work, leisure or other activities away from home. A large number of test devices and test systems are known that are based on the use of test elements in the form of test strips. Applications are known, in which a multiplicity of test strips is provided by a magazine, wherein a test strip from the magazine automatically may be provided to the testing device. Other applications, however, are known in which single test strips are used, which are inserted into the testing device manually by a user. For applying the sample to the test element, typical test elements provide at least one sample application site, such as a capillary opening in capillary test elements. Alternatively to home care applications, such test elements may be used in professional diagnostics, such as in hospital applications.

In many cases, for detecting the analyte, test elements are used, such as test strips, which comprise one or more test fields having one or more test chemistries. The test chemistries are adapted to change one or more detectable properties in the presence of the analyte to be detected. Thus, electrochemically detectable properties of the test chemistry and/or optically detectable properties of the test chemistry may be changed due to the influence of the presence of the analyte. For test chemistries that may be applied in the present disclosure, reference may be made to J. Hones et al.: Diabetes Technology and Therapeutics, Vol. 10, Supplement 1, 2008, S-10 to S-26.

In general, the detection of the at least one analyte can be performed by using an electrochemical test element. Herein, the test element typically comprises at least two separate electrodes connected to a suitable electronic circuit. Usually, at least one electrode, often designated as working electrode, is employed for detecting the analyte. For this purpose, the working electrode is usually covered with an electrochemical transducer configured for converting parameters with respect to the analyte into a measurable property of the electrode, in particular into an electrical current or an electrical potential. Typically, the working electrode comprises at least one detector reagent, in particular at least one enzyme, such as glucose oxidase (GOD), adapted to perform an oxidation reaction and/or a reduction reaction with the analyte. In case the detection reaction comprises an oxidation reaction at the working electrode, the counter electrode typically provides a reduction reaction in order to close the electric circuit through a measuring cell of the test element. For this purpose, the second electrode is designed in a manner that a maximum current detectable at the working electrode may pass the second electrode, thereby supporting a sufficient electrode reaction. From an application of disposable test elements for detecting an analyte concentration or a physiological activation time in a sample of a body fluid two distinct test strip configurations are known.

In a first known configuration, a test chemistry is used for covering the at least two electrodes in the test element. Herein, the two electrodes comprise the same material being selected from a noble metal, typically silver, or a carbon material. In this configuration, the test chemistry is adapted to support the analytical detection reaction at the working electrode and, at the same time, the electrode reaction at the counter electrode. As a result, a current can pass through the electrochemical test element. For purposes of producing the test element, the test chemistry is, generally, applied to the electrodes that are arranged in a co-planar manner and, subsequently, dried. During application of the test element, the test chemistry is then dissolved by the liquid sample comprising the body fluid, by which process the two electrodes become electrically connected. As described above, the electrochemical transducer is adapted to support the detection reaction. However, not all possible electrochemical transducers may simultaneously support the reaction at the counter electrode. Furthermore, particularly due to interfering reactions or insufficient reagent stability, some test chemistries cannot be combined with compounds that would otherwise be configured for supporting the counter electrode reaction.

Therefore, a second known configuration comprising the separated Ag/AgCl electrode as the counter electrode is, generally, employed with disposable test strip bio sensors. Herein, the at least two electrodes are located in a separated manner, covered with different kinds of reagents, and only connected by the sample comprising the body fluid, which works as a liquid electrolyte. In this configuration, a silver-silver chloride electrode (Ag/AgCl electrode) is used frequently. The Ag/AgCl electrode supports an anodic reaction

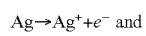

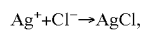

wherein, as a result of a precipitation of silver ions $Ag^+$ with chloride ions $Cl^-$, a coverage comprising silver chloride AgCl is obtained, or a cathodic reaction $$AgCl \rightarrow Ag^+ + Cl^- \text{ and}$$

$$Ag^+ + e^- \rightarrow Ag,$$

wherein silver ions $Ag^+$ are produced by dissolving the silver chloride AgCl, wherein the silver ions subsequently return to silver atoms on the negatively charged silver layer of the counter electrode. Accordingly, the electrical potential for this electrode reaction only depends on a chloride concentration of the electrolyte, which is for a blood sample quite constant. This type of electrode reaction that comprises a precipitation and a re-dissolving step provides a rather constant electrode potential that is, further, largely independent from the electrode current that may have a potential to depolarize the electrode.

Herein, the reagent layer on the working electrode may comprise an enzyme with a redox active enzyme co-factor to support a specific oxidation of the analyte in the body fluid. The reagent layer may comprise further a redox cycle providing substance, which may act as an electron acceptor. The redox cycle providing substance or redox mediator may react with the enzyme co-factor and may transport electrons taken from the enzyme co-factor to the electrode surface by diffusion. At the electrode surface, the redox mediator may be oxidized and the transferred electrons may be detected as a current, wherein the current may be proportional to a concentration of the analyte in the body fluid. Examples for this embodiment may be found in US 2003/0146113 A1 or US 2005/0123441 A1. As a further example, detection reagent test strips commercially available under the trade name COAGUCHEK XS test (Roche Diagnostics) for measuring a pro-thrombin activation time, comprise an artificial peptide substrate, wherein the protease thrombin may specifically cut off a linked redox tag. By applying a suitable voltage, the cleavage of the redox tag then can be detected by a resulting current. Herein, an Ag/AgCl electrode is used as the counter electrode.

However, known manufacturing processes for the Ag/AgCl electrode are associated with a number of disadvantages. Usually, a silver chloride material, such as in form of an ink or a paste, is coated or printed upon conductive traces in a manner that it may not react, such as by corrosion, with the material of the conductive traces, for which, in particular, a noble metal, including silver, or carbon is used. Unfavorably, silver chloride inks or pastes are rather expensive and the corresponding manufacturing process for producing the Ag/AgCl electrode is complex, in particular due to the steps involving coating and drying. Further, the silver chloride coatings exhibit a rough surface, thus, making it difficult to laminate the test strips layers together such that the laminated test strips exhibit sufficient stability.

Furthermore, silver chloride inks or pastes are electrically conductive. Therefore, the resulting electrode structures may be short cut after coating as a stripe over the structured co-planar electrodes. To avoid this disadvantage, the strips may be coated, such as by a reel-to-reel process, at a position where only one conductive pathway stays in contact with the silver chloride paste or ink. This, however, can only be performed at the dosing side of the test strip. For example, in case of the above-mentioned COAGUCHEK XS test strip (Roche Diagnostics), in which a long sample capillary is used in order to be able to move the sample to a heater position located within the meter, the Ag/AgCl counter electrode, thus, remains far away from the working electrode and, particularly, outside a thermostatically controlled test zone. In order to place the Ag/AgCl electrode at a different position, the paste or ink must be limited to the electrode surface so that a pure reel-to-reel process will not be applicable.

Alternatively, a direct structuring of a layer of the silver chloride material in order to form at least one surface of the Ag/AgCl electrode, conductive pathways, and contact pads is also feasible. Depending on a nature of the selected structuring process, this kind of procedure which involves a local printing process could significantly increase the cost of the production and, concurrently, reduce production rate and production robustness.

A further known process for producing a silver chloride layer on a silver surface comprises an anodic polarization of a silver coated polymer foil in an electrolyte comprising chloride ions. This process, however, requires an electrolyte bath and a corresponding electrical contact during the production process. As a result, the typical reel-to-reel process, which allows producing test strips over a length of more than 500 m, is again not applicable here.

WO 2003/076648 A1 discloses such a manufacturing process for an Ag/AgCl electrode, wherein, prior to coating the silver electrode with a polymer film in order to immobilize a redox mediator and an enzyme, an anodic current is conducted through the silver electrode which is placed in a solution comprising chloride ions, by which step a thin silver chloride layer is obtained on a surface of the Ag electrode.

US 2009/0294306 A1 and US 2009/0298104 A1 each disclose a method for an in-situ renewal of the AgCl layer of an Ag/AgCl reference electrode, wherein the Ag/AgCl reference electrode has been produced before by a method according to the state of the art, such as the method described in US 2006/0016700 A1. Herein, a level of silver chloride on the Ag/AgCl reference electrode of an electrochemical sensor, which is subcutaneously implanted in a patient, is replenished by applying a brief electrical potential across the reference electrode and another electrode for a period of time being sufficient for converting silver to silver chloride in order to replenish the level of silver chloride present on the reference electrode in order to maintain a stable potential over the lifetime of the implanted electrochemical sensor. Accordingly, only the $Ag^+$ ions which are initially generated in small amounts by a naturally-occurring dissolution of the AgCl layer are converted into additional silver chloride which is, subsequently, deposited onto the still existing AgCl layer of the reference electrode.

US 2002/0112969 A1 and EP 1 343 007 A1 each disclose a method for a generation of an AgCl layer, wherein $Ag^+$ ions are generated in small amounts by a naturally-occurring dissolution of an Ag layer without application of an electrical potential. Accordingly, by using negatively charged $Cl^-$ ions being present in the body fluid the generated positively charged $Ag^+$ ions may, thus, form a AgCl precipitation, however, only to a minor degree.

U.S. Pat. No. 6,153,069 A discloses a method for an in-situ generation of an AgCl layer on a silver electrode, wherein, in a specific embodiment, suitable reactants, such as ferricyanides, are used to initially generate the $Ag^+$ ions which may, without application of an electrical potential, subsequently react with $Cl^-$ ions being present in the sample fluid in order to form a silver chloride (AgCl) precipitation. In a further embodiment, an Ag/AgCl electrode is initially generated by depositing a silver oxide layer through reactive sputtering onto an Ag film. During subsequent testing, the silver oxide layer is, without application of an electrical potential, converted in-situ into silver chloride when the test element contacts the body fluid comprising chloride ions.

SUMMARY

It is against the above background that the present disclosure provides certain unobvious advantages and advancements over the prior art. In particular, the inventors have recognized a need for improvements in methods and test elements for electrochemically detecting at least one analyte in a sample of a body fluid.

Although the embodiments of the present disclosure are not limited to specific advantages or functionality, it is noted that the present disclosure provides a method and a test element for electrochemically detecting at least one analyte in a sample of a body fluid, which can be manufactured in an easy and cost effective process, thereby avoiding at least some of the disadvantages associated with the production process according to the state of the art.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e., a situation in which A solely and exclusively consists of B) and to a situation in which, besides B, one or more further elements are present in entity A, such as element C, elements C and D or even further elements.

Further, as used in the following, the terms "typically", "more typically", "preferably", "more preferably", "particularly", "more particularly", "specifically", "more specifically" or similar terms are used in conjunction with optional features, without restricting alternative possibilities. Thus, features introduced by these terms are optional features and are not intended to restrict the scope of the claims in any way. The embodiments of the present disclosure may, as the skilled person will recognize, be performed by using alternative features. Similarly, features introduced by "in an embodiment of the disclosure" or similar expressions are intended to be optional features, without any restriction regarding alternative embodiments of the disclosure, without any restrictions regarding the scope of the embodiments of the disclosure, and without any restriction regarding the possibility of combining the features introduced in such a way with other features of the disclosure.

In accordance with one embodiment of the present disclosure, a method for generating a layer of silver chloride at a surface of an electrode of a test element is provided, the method comprising the steps: a') providing the at least one test element, wherein the test element comprises at least one first electrode and at least one second electrode, wherein the first electrode contacts a test chemistry, wherein the test chemistry is or comprises a redox mediator in an oxidized form, and wherein a surface of the second electrode consists of silver metal; b') contacting at least the surface of the second electrode with a sample of a body fluid comprising chloride ions; and c) applying a first voltage ($V_1$) between the first electrode as a cathode and the second electrode as an anode for a time and with a voltage sufficient for forming a layer of silver chloride at the surface of the second electrode, wherein the oxidized form of the redox mediator is transformed into a reduced form.

In accordance with another embodiment of the present disclosure, a method for electrochemically detecting at least one analyte in a sample of a body fluid comprising chloride ions is provided, the method comprising the steps: a) providing at least one test element, wherein the test element comprises at least one first electrode contacting a test chemistry and at least one second electrode, wherein the test chemistry is or comprises a redox mediator in an oxidized form, wherein, in an absence of the sample, a surface of the second electrode adapted to contact the sample of the body fluid consists of silver metal; b) contacting both the first electrode and the second electrode with the sample of the body fluid comprising the chloride ions; c) applying a first voltage ($V_1$) between the first electrode as a cathode and the second electrode as an anode for a time and with a voltage sufficient for forming a layer of silver chloride at the surface of the second electrode, wherein the oxidized form of the redox mediator is transformed into a reduced form; d) applying a second voltage ($V_2$) between the first electrode as the anode and the second electrode as the cathode; and e) determining an electrical signal between the first electrode and the second electrode, whereby the analyte in the sample of the body fluid comprising the chloride ions is detected, wherein detecting the analyte comprises re-oxidizing the redox mediator.

In accordance with yet another embodiment of the present disclosure, a system for determining at least one property of a sample of a body fluid comprising chloride ions is provided, the system comprising at least one test element for electrochemically detecting at least one analyte in a sample of a body fluid comprising chloride ions, wherein the test element comprises at least one first electrode contacting a test chemistry, wherein the test chemistry is or comprises a redox mediator in an oxidized form, and at least one second electrode, wherein, in an absence of the sample, a surface of the second electrode adapted to contact the sample consists of silver metal, the system further comprising at least one measurement device configured for performing at least one electrical measurement by using the test element, wherein the measurement device is used to apply a first voltage ($V_1$) between the first electrode as a cathode and the second electrode as an anode for a time and with a voltage sufficient for forming a layer of silver chloride at the surface of the second electrode.

These and other features and advantages of the embodiments of the present disclosure will be more fully understood from the following detailed description taken together with the accompanying claims. It is noted that the scope of the claims is defined by the recitations therein and not by the specific discussions of features and advantages set forth in the present description.

BRIEF DESCRIPTION OF THE DRAWINGS

The following detailed description of the embodiments of the present disclosure can be best understood when read in conjunction with the following drawings, where like structure is indicated with like reference numerals and in which:

FIG. 1A and FIG. 1B show a schematic representation of the method for electrochemically detecting at least one analyte in a sample of a body fluid according to the present disclosure using a typical embodiment of a test element during a preparation phase (FIG. 1A) and a detection phase (FIG. 1B);

Figure 2:
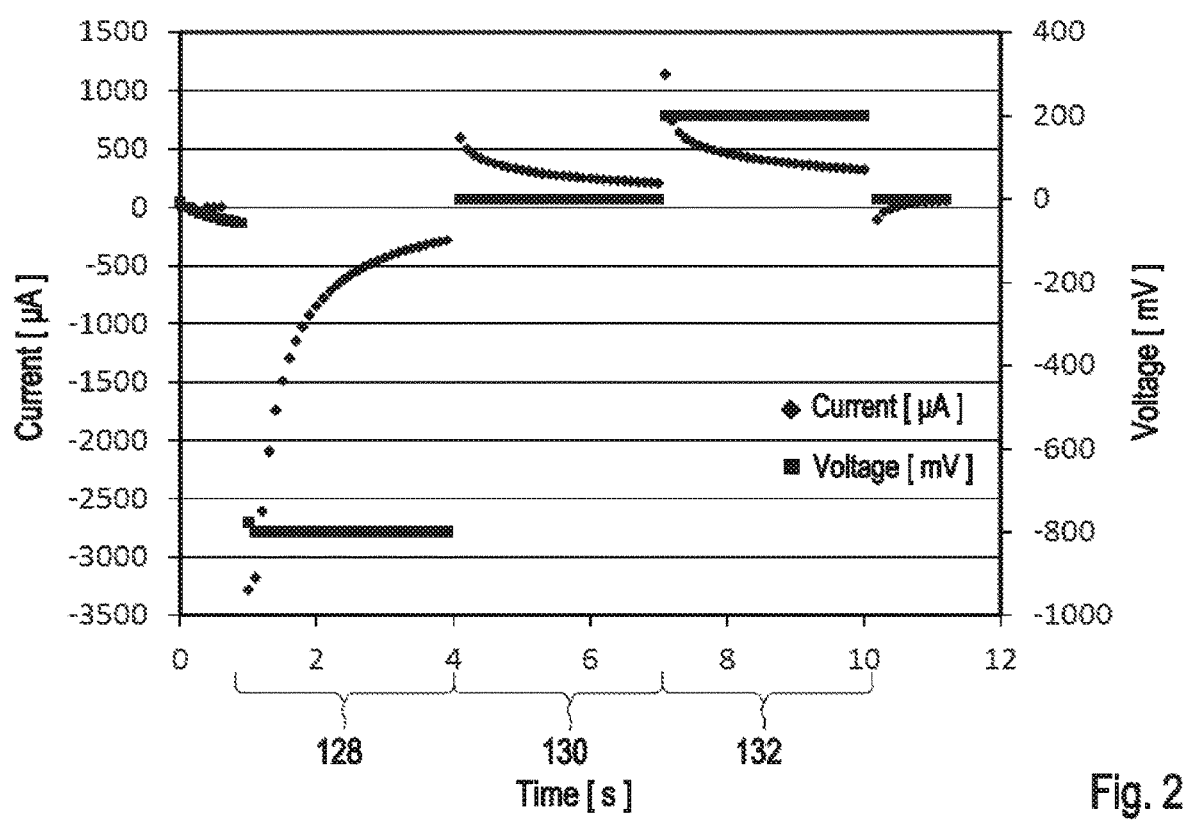
FIG. 2 shows experimental results of a current response during the preparation phase, an optional stationary phase and the detection phase.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiments of the present disclosure.

DETAILED DESCRIPTION

In a first aspect of the present disclosure, a method for generating a layer of silver chloride at a surface of an electrode of a test element is disclosed, wherein the method comprises the following steps:

a') providing the at least one test element, wherein the test element comprises at least one first electrode and at least one second electrode, wherein the first electrode contacts a test chemistry, wherein the test chemistry is or comprises a redox mediator in an oxidized form, wherein a surface of the second electrode consists of silver metal;

b') contacting at least the surface of the second electrode with a sample of a body fluid comprising chloride ions; and c) applying a first voltage between the first electrode as a cathode and the second electrode as an anode for a time and with a voltage sufficient for forming a layer of silver chloride at the surface of the second electrode, wherein the oxidized form of the redox mediator is transformed into a reduced form.

Herein, the indicated steps may, typically, be performed in the given order, starting with step a'). However, any or all of the indicated steps, in particular steps b') and c), may also be preformed at least partially concurrently, such as over a definite period of time, and/or repeated several times. It is further emphasized that steps a') and b') are denominated in the indicated manner since they exhibit similar features compared to steps a) and b) as described below in the method for electrochemically detecting at least one analyte in the sample of the body fluid, whereas the denomination of step c) indicates that it exhibits identical features for both methods as addressed here.

According to step a'), the test element comprises at least one first electrode and at least one second electrode. As used herein, the term "test element" refers to an arbitrary device being capable of detecting an analyte in a body fluid, typically by comprising at least one component that may alter at least one detectable property when the analyte is present in the body fluid, such as a test chemistry, such as one or more of the test chemistries as described in the Background. The test element may, additionally, comprise at least one reference electrode, for example a combined counter electrode/reference electrode system. In particular, the test element used for the present disclosure may, typically, be a disposable, single-use test element, typically in form of a test strip as described below in more detail.

Further, the term "electrode" refers to an entity of the test element which is adapted to contact the body fluid, either directly or via at least one semipermeable membrane or layer. Each electrode may be embodied in a manner that an electrochemical reaction may take place at at least one surface of the electrode. Thus, the electrodes may be embodied in a manner that an oxidation reaction and/or a reduction reaction occur at the electrodes. The first electrode and the second electrode may have the same dimension, wherein the term "dimension" refers to one or more of a width, a length, a surface area, a shape of the first and the second electrodes. In particular, the first and the second electrodes may be designed with a non-structured electrode shape, such as a shape without structures such as inlets, notches, etc. The shape of the electrodes may be determined by a manufacturing process, such as a cutting process. Thus, the shape may be essentially rectangular wherein the term "essentially rectangular" indicates that deviations from a rectangular shape may be possible within tolerances of manufacturing. As used herein, the term "surface" of the electrode refers to an area on the electrode, typically exhibiting an essentially rectangular shape, which is adapted to contact, typically directly, one or more samples.

According to an embodiment of the present disclosure, the second electrode exhibits a metallic silver surface, wherein the silver surface is adapted to contact the at least one sample which comprises at least one body fluid. As a result, the surface of the second electrode consists of silver metal which is, thus, arranged in order to directly contact the at least one body fluid. As used herein, the term "silver metal" refers to the chemical element silver in occurrence in an elementary form. This is in contrast to silver ions that may easily be ready to enter into a compound, such as a salt, with another chemical element. Accordingly, the second electrode may be a massive silver electrode or, particularly due to considerably reduced material expenses, typically, comprise a metallic silver layer that may be disposed on a second electrode carrier layer, typically a second electrode carrier foil. In a typical embodiment, the silver layer may fully cover the second electrode carrier layer. In this embodiment, a width of the silver layer corresponds to a width of the second electrode carrier layer, wherein the term "width" of the silver layer and of the second electrode carrier layer refers to a maximum extension perpendicular to an elongated test element direction. More details concerning the second electrode are described below.

According to step b'), at least the surface of the second electrode gets into contact with the sample of the body fluid. As used herein, the term "body fluid" refers to a fluid constituent being present in a body tissue of the patient, such as in an interstitial tissue. Thus, the sample of the body fluid may, typically, be selected from a group consisting of blood, in particular whole blood; plasma; serum, urine; saliva; or an interstitial fluid. However, additionally or alternatively, one or more other types of other body fluids or derivatives of these body fluids may be used.

According to an embodiment of the present disclosure, the body fluid being used for getting into contact with the second electrode comprises chloride ions. This is the case for all of the mentioned typical body fluids as chloride is present in a human body since it is required for both metabolism and maintaining an acid-base balance of the body. As an example, the blood plasma of a healthy adult person comprises an amount of chloride in form of a quite constant concentration within a range from 95 mmol/L to 110 mmol/L.

As a result of step b'), at least a small amount of the chloride ions which are provided by the sample of the body fluid are likely to approach the surface of the second electrode. However, as long as no appropriate electrical potential is applied across the two electrodes comprised within the test element, the consequences will be negligible. Therefore, according to step c) of the present disclosure, a first voltage is applied between the first electrode as a cathode and the second electrode as an anode with a voltage which is known for the skilled person to be sufficient for forming a layer of silver chloride at the surface of the second electrode. In a particularly typical embodiment, a measurement device that may be adapted to interact with the test element may be also used in order to apply any voltages, in particular but not limited to the first voltage, between the first electrode and the second electrode. For this purpose, the test element may, in particular, be inserted into the measurement device which will be described below in more detail.

Thus, the appropriate electrical potential may, initially, cause a production of silver ions, wherein the silver ions may, in particular due to their opposite charge, congregate with the chloride ions available within the sample of the body fluid in order to form silver chloride, which may, subsequently precipitate as a layer of silver chloride at the surface of the second electrode. As known to the skilled person, an increase of a thickness of the silver chloride layer may result in a decrease of the current through the respective electrode. As a result, the precipitation of the silver chloride layer may decrease and, finally, be terminated after a specific time which may, generally, last from 0.2 s to 10 s, typically from 0.5 s to 5 s, such as from 1 s to 1.5 s, after having started an application of the appropriate electrical potential.

Consequently, it might be particularly typical when the time during which the first voltage is applied between the first electrode and the second electrode may be selected from a time interval having a lower limit and an upper limit. Herein, the lower limit for applying the first voltage in this manner may be selected from a time of at least 0.2 s, typically of at least 0.5 s, more typically of at least 1 s. Further, the upper limit may, typically, be defined in a fashion that the application of the first voltage between the first electrode and the second electrode may, typically, be terminated after a measured current may have decreased to or is approaching a stable current level, in particular to a stable low current level. As used herein, the term "stable current level" may refer to a set of subsequently measured current values, which exhibit relative differences between them that are below a selected threshold, in particular below the differences between subsequently measured current values that are outside the stable current level. As has been found by experimental investigations, the upper limit for applying the first voltage in this manner may, thus, typically be selected from a time of at least 1.5 s, 2 s, 3 s, 5 s, or 10 s. Thus, instead of generating the Ag/AgCl electrode according to the state of the art already during the production process, the layer of the silver chloride is produced within the test element by applying at least one suitable voltage during at least one selected time interval when wetted with the liquid sample, which comprises chloride ions.

As a result of the application of the first voltage in the described manner, a flow of an electrical current is generated through both the first electrode and the second electrode at the test element. Hereby, an anodic polarization of the silver layer, i.e., a silver oxidation $$Ag \rightarrow Ag^+ + e^-,$$

as comprised at least at the surface of the second electrode is performed. The chloride ions that precipitate into the desired silver chloride layer according to the equation $$Ag^+ + Cl^- \rightarrow AgCl$$

are provided by the liquid sample of the body fluid, in particular the blood sample. To maintain the electrical current through both the first and the second electrode of the test element, the first electrode, typically, provides a complementary electrochemical reduction process $$S_{ox} + e^- \rightarrow S_{red},$$

wherein S denotes a reducible substance in an oxidized form $S_{ox}$ and in an reduced form $S_{red}$, respectively. Therefore, the first electrode may be coated with a reagent layer comprising a suitable reducible substance.

In a particularly typical embodiment, the first electrode contacts a test chemistry, wherein the test chemistry may be or comprise a redox mediator in an oxidized form. As used herein, the term "redox mediator" refers to one or more molecules or complex compounds that are configured to assist in charge transfer by being an electron acceptor in a first location, where electrons are produced, and an electron shuttle in a transfer of electrons from the first location to a second location, where electrodes are used to effect further reactions. During this transfer, the redox mediator may be altered by receiving and releasing one or more electrons, in particular by exerting an electrical force upon the redox mediator, such as by an electrical potential. In the present disclosure, the oxidized form of the redox mediator may, thus, be transformed into a reduced form of the redox mediator during step c) by applying the first voltage between the first electrode as the cathode and the second electrode as the anode for the time and with the voltage as indicated above. As a result, the redox mediator may be used here for two different roles, namely as the reducible substance in the method for generating the layer of silver chloride and, concurrently, as a substance involved in the detection step in the method for detecting the analyte as described below.

In a further aspect of the present disclosure, a method for generating for electrochemically detecting at least one analyte in a sample of a body fluid comprising chloride ions is disclosed, wherein the method comprises the following steps:

a) providing at least one test element, wherein the test element comprises at least one first electrode contacting a test chemistry and at least one second electrode, wherein the test chemistry is or comprises a redox mediator in an oxidized form, wherein, in an absence of the sample, a surface of the second electrode adapted to contact the sample of the body fluid consists of silver metal;

b) contacting both the first electrode and the second electrode with the sample of the body fluid comprising the chloride ions;

c) applying a first voltage between the first electrode as a cathode and the second electrode as an anode for a time and with a voltage sufficient for forming a layer of silver chloride at the surface of the second electrode, wherein the oxidized form of the redox mediator is transformed into a reduced form;

d) applying a second voltage between the first electrode as the anode and the second electrode as the cathode; and e) determining an electrical signal between the first electrode and the second electrode, whereby the analyte in the sample of the body fluid comprising the chloride ions is detected, wherein detecting the analyte comprises re-oxidizing the redox mediator.

Herein, the indicated steps may, typically, be performed in the given order, starting with step a). However, any of the indicated steps, in particular steps b) and c), on one hand, and steps d) and e), on the other hand, may also be preformed at least partially concurrently, such as over a definite period of time, and/or repeated several times. As already mentioned above, steps a) and b) exhibit similar properties compared to steps a') and b') as described above in the method for generating the layer of the silver chloride, while step c) exhibits identical features for both methods addressed here. Whereas steps a) to c) are used for generating the layer of the silver chloride as described above and may, thus, be denominated as a "preparation phase", the further steps d) and e) of the present method are applied for detecting the analyte in the sample of the body fluid by using the layer of the silver chloride as provided by steps a) to c) and may, therefore, be denominated as a "detection phase". Therefore, with respect to the preparation phase, reference may also be made to the description above.

As used herein, the term "analyte" may refer to an arbitrary element, component or compound being present in the body fluid and the concentration of which may be of interest for a user or a patient. Typically, the analyte may be or may comprise an arbitrary chemical substance or chemical compound which may take part in the metabolism of the patient, such as at least one metabolite. As an example, the at least one analyte may be selected from the group consisting of glucose, cholesterol, triglycerides, and lactate. Additionally or alternatively, however, other types of analytes may be used and/or any combination of analytes may be determined. As generally used herein, the term "patient" may refer to a human being or an animal, independent from the fact that the human being or animal, respectively, may be in a healthy condition or may suffer from one or more diseases. As an example, the patient may be a human being or an animal suffering from diabetes. However, additionally or alternatively, the embodiments of the present disclosure may be applied to other types of users or patients.

The difference between steps a') and b'), on one hand, and steps a) and b), on the other hand, indicates that for detecting the analyte in the sample of the body fluid the first electrode is adapted to contact the body fluid and, for this purpose, contacts the test chemistry. Herein, the term "test chemistry" refers to an arbitrary material or a composition of materials adapted to change at least one detectable property in the presence of the at least one analyte. Generally, this property may be selected from an optically detectable property, such as a color change and/or a change in remissive properties, and/or an electrochemically detectable property. As used herein, the term "electrochemically detection" refers to a detection of an electrochemically detectable property of the analyte, such as an electrochemical detection reaction. Thus, the electrochemical detection reaction may, typically, be detected by comparing one or more electrode potentials, in particular an electrostatic potential of the first electrode with the electrostatic potential of one or more further electrodes such as the second electrode or a reference electrode.

For test chemistries, reference may be made to the Background section above. Specifically, the at least one test chemistry may be a highly selective test chemistry, which only changes the property if the analyte is present in the sample of the body fluid applied to the test element, whereas no change occurs if the analyte may not be present. More typically, the degree or change of the at least one property may be dependent on the concentration of the analyte in the body fluid, in order to allow for a quantitative detection of the analyte. Herein, the test chemistry may comprise one or more enzymes, such as glucose oxidase (GOD) and/or glucose dehydrogenase (GDH), typically an enzyme which, by itself and/or in combination with other components of the detector substance, is adapted to perform an oxidation and/or reduction reaction with the at least one analyte to be detected. Additionally or alternatively, the test chemistry may comprise one or more auxiliary components, such as one or more co-enzymes and/or may comprise one or more redox mediators as mentioned above. Additionally, the test chemistry may comprise one or more dyes, which, typically in interaction with the one or more enzymes, may change their color in the presence of the at least one analyte to be detected.

Typically, the first electrode may comprise at least one electrode conductive layer and at least one test chemistry in contact with the first electrode conductive layer. Herein, the term "electrode conductive layer" refers to a layer with electrically conductive properties, wherein the term "electrically conductive" describes an electric conductivity, typically given in S/m or 1/Ωm, of at least $10^0$ S/m, typically of at least $10^3$ S/m and, more typically, of at least $10^5$ S/m. The first electrode conductive layer may comprise at least one of: a metal layer, in particular a noble metal layer selected from the group consisting of palladium, silver or gold; a conductive carbon layer, in particular a carbon paste layer. As further used herein, the term "paste" refers to an amorphous substance containing one or more particulate components, such as one or more conductive components and/or powders, as well as one or more binder materials, such as one or more organic binder materials. Additionally or alternatively, the first electrode conductive layer may comprise an aluminum layer, such as a sputtered aluminum layer, combined with a conductive carbon paste.

According to another embodiment of the present disclosure, during the detection phase according to steps d) and e), a second voltage is applied between the first electrode as the anode and the second electrode as the cathode and an electrical signal between the first electrode and the second electrode is determined. With respect to the difference between the first voltage as applied during step c) and the second voltage as applied during step d), it is emphasized that by each step an appropriate electrical potential across the two electrodes is provided but in two opposing directions, respectively. Thus, after step c) but before step d) the polarity of the applied voltage may be switched into the opposite direction. For this purpose, it may be advantageous to disconnect both the first electrode and the second electrode from the polarization over a period of time, typically over a duration lasting for 0.5 to 30 seconds, more typically for 3 to 10 seconds, wherein the period of time may be denominated as an optional "stationary phase", before reconnecting again for applying the second voltage. During the stationary phase, the redox mediator, which may be present in the reduced form after step c) may, thus, be able to diffuse away from the surface of the first electrode.

After switching the polarity of the applied voltage during a transition from step c) to step d), the redox mediator in the reduced form may, typically, be re-oxidized at the first electrode, thereby being used in detecting the analyte according to step e). For this purpose, the redox mediator may be provided in a reduced form with the detection reagent so that it can take the electrons from an enzymatic reaction with the analyte and transport the electrons to the first electrode, such as by means of a diffusion process. At the first electrode, the reduced redox mediator might become re-oxidized when a sufficient voltage is applied between the electrodes. In order to provide a flow of the electrical current between the two electrodes during step e), the silver ions in the silver chloride layer at the first electrode become reduced to silver atoms, whereby the silver ions may be replaced by a dissociation of the silver chloride, a layer of which was produced during the preparation phase.

In accordance with yet another embodiment of the present disclosure, a test element for electrochemically detecting at least one analyte in a sample of a body fluid comprising chloride ions is disclosed. As already described above, the test element comprises at least one first electrode contacting a test chemistry, wherein the test chemistry is or comprises a redox mediator in an oxidized form, and at least one second electrode, wherein, in an absence of the sample, a surface of the second electrode adapted to contact the body fluid comprises silver. As described above, the second electrode may be a massive silver electrode or, typically, comprise a silver layer disposed on a second electrode carrier layer, typically a second electrode carrier foil. For this purpose, the second electrode carrier foil may comprise a polymer foil, in particular a silver-sputtered polyester foil, on which the silver layer comprises a thickness in a range from 10 nm to 1000 nm, typically from 50 nm to 250 nm.

The test element may further comprise at least one capillary, which may be adapted to receive the sample. As used herein, the term "capillary" refers to an element being adapted to receive the sample of the body fluid and/or transport the sample of the body fluid by capillary forces. The capillary element may comprise at least one volume configured to receive the sample of the body fluid, e.g., one or more capillary caps and/or one or more capillary slots and/or one or more capillary tubes having an arbitrary cross-section, such as a rectangular cross-section and/or a rounded cross-section and/or a polygonal cross-section.

In a particularly typical embodiment, the first electrode and the second electrode may be arranged on opposing sides of the capillary, such that a surface of the first electrode faces a surface of the second electrode. The first electrode and the second electrode may be aligned in parallel, in particular as surfaces that are parallel to each other at least in the direction defined by the length of the capillary. Further, as outlined above, the first and the second electrode may have the same dimensions and may have a non-structured shape. In addition, both the first electrode and the second electrode may extend over a full length of the capillary. As used herein, the term "length of the capillary" refers to a maximum extension of the capillary in one dimension within the test element. Further, the test element may comprise a first electrode contact zone and a second electrode contact zone adapted to contact the first electrode and the second electrode with a further device, in particular a measurement device as described below.

In accordance with still yet another embodiment of the present disclosure, a method for producing the test element as described above or below is disclosed. Accordingly, the method comprises providing at least one first electrode contacting a test chemistry, wherein the test chemistry is or comprises a redox mediator in an oxidized form, and at least one second electrode, wherein a surface of the second electrode adapted to contact the body fluid comprises silver. The first electrode, the second electrode and the capillary may, typically, be formed such that the first electrode and the second electrode are arranged on opposing sides of the capillary. Herein, it may particularly be typical to depose the silver as a thin film or a layer on a substrate, typically by sputtering silver on a polymer substrate, in particular on a polyester foil, in a manner that the silver layer acquires a thickness in a range from 10 nm to 1000 nm, typically in a range from 50 nm to 250 nm.

The test element may be produced in a continuous process. As used herein, the term "continuous process" refers to an arbitrary process in which, by contrast with batch-to-batch processes, production proceeds successively and without interruption of a supporting tape, e.g., a carrier tape. The continuous process may be a reel-to-reel process. For example, the supporting tape may be provided from a starting roller and may be wound up onto a further roller after laminating further tapes onto it.

Further, the method may comprise cutting the test element into test strips. As used herein, the term "strips" refers to an element having an elongated shape and a thickness, wherein an extension of the element in a lateral dimension exceeds the thickness of the element, such as by at least a factor of 2, typically by at least a factor of 5, more typically by at least a factor of 10, and most typically by at least a factor of 20 or more. Thus, the test element may be a test strip. The term "cutting" may comprise dividing the laminated tape into separated test strips, such that the separated test strips may be used individually.

In accordance with yet still another embodiment of the present disclosure, a system for determining at least one property of a sample of a body fluid comprising chloride ions is disclosed. The system comprises at least one test element as disclosed above or below in further detail. The system further comprises at least one measurement device adapted for performing at least one electrical measurement by employing the test element. As used herein, the term "determining at least one property" refers to detecting at least one analyte in the body fluid. As used herein, the term "measurement device" refers to an arbitrary device, typically to an electronic device, which may be handled independently from the test element. The measurement device may be adapted to interact with the test element in order to detect the at least one signal produced by one of the first and second electrode and to apply a voltage to the other one of the first and second electrode. The measurement device further may be adapted to derive at least one item of information regarding the presence and/or concentration of the analyte in the sample of the body fluid from this detection. For this purpose, the measurement device may comprise at least one electronic evaluation device interacting with the first and second electrodes, in order to derive the at least one information and/or concentration of the at least one analyte from the at least one signal. Thus, the measurement device may comprise at least one evaluation unit comprising at least one data processing device, such as a microcontroller.

The measurement device may be configured to perform at least one impedance measurement using the first electrode and the second electrode. The measurement device may be further configured to perform at least one amperometric measurement using the first electrode and the second electrode, in particular to detect an AC signal and/or a DC signal. For this purpose, the measurement device may be configured to apply an AC signal to the first electrode and to the second electrode and to detect, in particular continuously, a response.

The measurement device may be configured to perform at least one initial failsafe measurement before applying the sample of the bodily fluid. The failsafe measurement may comprise at least one electrical measurement using the first electrode and the second electrode. The electrical measurement may be used for deriving at least one electrical measurement value, wherein the failsafe measurement may further comprise comparing the electrical measurement value with at least one threshold value. The failsafe measurement may comprise detecting at least one damage and/or deterioration of the at least one of the conductive layers of the first electrode and/or or the second electrode.

The present disclosure is particularly advantageous in its generating the silver chloride layer at the surface of the second electrode of the test element. Whereas, usually, a silver chloride material, in particular in form of an ink or a paste, is coated or printed upon a conductive layer of the second electrode as a manufacturing step at the production site of the test element, the present embodiment of the disclosure provides a different method for providing the silver chloride layer. Consequently, no silver chloride-comprising ink or paste is required to be disposed upon the conductive layer of the second electrode, thus, allowing manufacturing of the test element in an easier and more cost effective process.

In addition, the method for generating a layer of silver chloride at a surface of an electrode of a test element according to the present disclosure may also be applied in other kinds of test elements in which a silver chloride layer may be used. A particularly typical example may refer to the COAGUCHEK XS test (Roche Diagnostics) in which a reference/counter electrode coated with a silver chloride layer is employed.

Summarizing the findings of the present disclosure, the following embodiments are typical:

Embodiment 1

A method for generating a layer of silver chloride at a surface of an electrode of a test element, the method comprising the steps:
  a') providing the at least one test element, wherein the test element comprises at least one first electrode and at least one second electrode, wherein the first electrode contacts a test chemistry, wherein the test chemistry is or comprises a redox mediator in an oxidized form, wherein a surface of the second electrode consists of silver metal;
  b') contacting at least the surface of the second electrode with a sample of a body fluid comprising chloride ions; and
  c) applying a first voltage between the first electrode as a cathode and the second electrode as an anode for a time and with a voltage sufficient for forming a layer of silver chloride at the surface of the second electrode, wherein the oxidized form of the redox mediator is transformed into a reduced form.

Embodiment 2

The method according to the preceding embodiment, wherein a measurement device adapted to interact with the test element is used to apply the first voltage between the first electrode and the second electrode.

Embodiment 3

A method for electrochemically detecting at least one analyte in a sample of a body fluid comprising chloride ions, the method comprising the steps:
  a) providing at least one test element, wherein the test element comprises at least one first electrode contacting a test chemistry and at least one second electrode, wherein the test chemistry is or comprises a redox mediator in an oxidized form, wherein, in an absence of the sample, a surface of the second electrode adapted to contact the sample of the body fluid consists of silver metal;
  b) contacting both the first electrode and the second electrode with the sample of the body fluid comprising the chloride ions;
  c) applying a first voltage between the first electrode as a cathode and the second electrode as an anode for a time and with a voltage sufficient for forming a layer of silver chloride at the surface of the second electrode, wherein the oxidized form of the redox mediator is transformed into a reduced form;
  d) applying a second voltage between the first electrode as the anode and the second electrode as the cathode; and
  e) determining an electrical signal between the first electrode and the second electrode, whereby the analyte in the sample of the body fluid comprising the chloride ions is detected, wherein detecting the analyte comprises re-oxidizing the redox mediator.

Embodiment 4

The method according to the preceding embodiment, wherein a measurement device adapted to interact with the test element is used to apply the first voltage and/or the second voltage between the first electrode and the second electrode.

Embodiment 5

The method according to any one of the two preceding embodiments, wherein the time during which the first voltage is applied between the first electrode as the cathode and the second electrode as the anode during step c) is at least 0.2 s Embodiment 6

The method according to any one of the three preceding embodiments, wherein applying the first voltage is terminated after step c) and a period of time passes before the second voltage is applied according to step d).

Embodiment 7

The method according to the preceding embodiment, wherein the period of time comprises a value in a range from 0.5 to 30 seconds.

Embodiment 8

The method according to the preceding embodiment, wherein the period of time comprises a value in a range from 3 to 10 seconds.

Embodiment 9

The method according to any one of the preceding embodiments, wherein the second electrode comprises a silver layer being disposed on a second electrode carrier layer, wherein the second electrode carrier layer comprises a second electrode carrier foil.

Embodiment 10

The method according to the preceding embodiment, wherein the silver layer comprises of a thickness in a range from 10 nm to 1000 nm.

Embodiment 11

The method according to the preceding embodiment, wherein the silver layer comprises of a thickness in a range from 50 nm to 250 nm.

Embodiment 12

The method according to any one of the preceding embodiments, wherein the sample of the body fluid comprises blood, typically whole blood, plasma, serum, urine, saliva, or an interstitial fluid.

Embodiment 13

A test element for electrochemically detecting at least one analyte in a sample of a body fluid comprising chloride ions, wherein the test element comprises at least one first electrode contacting a test chemistry, wherein the test chemistry is or comprises a redox mediator in an oxidized form, and at least one second electrode, wherein, in an absence of the sample, a surface of the second electrode adapted to contact the sample consists of silver metal.

Embodiment 14

The test element according to the preceding embodiment, wherein the first electrode comprises at least one first electrode conductive layer, wherein the test chemistry is in contact with the first electrode conductive layer.

Embodiment 15

The test element according to the preceding embodiment, wherein the first electrode conductive layer comprises at least one of: a metal layer, typically a noble metal layer selected from the group consisting of palladium, platinum,—or gold; a conductive carbon layer, in particular a carbon paste layer.

Embodiment 16

The test element according to any one of the two preceding embodiments, wherein the first electrode conductive layer is disposed on a first electrode carrier layer, typically a first electrode carrier foil.

Embodiment 17

The test element according to the preceding embodiment, wherein the first electrode conductive layer fully covers the first electrode carrier layer.

Embodiment 18

The test element according to any one of the five preceding embodiments, wherein the second electrode comprises a silver layer being disposed on a second electrode carrier layer, wherein the second electrode carrier layer comprises a second electrode carrier foil, wherein the silver layer comprises of a thickness in a range from 10 nm to 1000 nm.

Embodiment 19

The test element according to the preceding embodiment, wherein the silver layer comprises of a thickness in a range from 10 nm to 1000 nm.

Embodiment 20

The test element according to the preceding embodiment, wherein the silver layer comprises of a thickness in a range from 50 nm to 250 nm.

Embodiment 21

The test element according to the preceding embodiment, wherein the second electrode carrier layer comprises a second electrode carrier foil.

Embodiment 22

The test element according to the preceding embodiment, wherein the second electrode carrier foil comprises a polymer foil, in particular a silver-sputtered polyester foil.

Embodiment 23

The test element according to any one of the five preceding embodiment, wherein the silver layer fully covers the second electrode carrier layer.

Embodiment 24

The test element according to any one of the preceding embodiments referring to the test element, further comprising at least one capillary adapted to receive the sample, wherein the first electrode and the second electrode are arranged on opposing sides of the capillary.

Embodiment 25

The test element according to the preceding embodiment, wherein the first electrode extends over a full length of the capillary.

Embodiment 26

The test element according to any one of the two preceding embodiments, wherein the second electrode extends over a full length of the capillary.

Embodiment 27

The test element according to any one of the preceding embodiments referring to the test element, wherein the test element is a test strip.

Embodiment 28

The test element according to any one of the preceding embodiments referring to the test element, wherein the test element comprises a first electrode contact zone and a second electrode contact zone configured to contact the first electrode and the second electrode with a further device, in particular a measurement device.

Embodiment 29

A method for producing a test element according to any one of the preceding embodiments referring to the test element, wherein the method comprises providing at least one first electrode contacting a test chemistry, wherein the test chemistry is or comprises a redox mediator in an oxidized form, and at least one second electrode, wherein a surface of the second electrode adapted to contact the sample consists of silver metal.

Embodiment 30

The method according to the preceding embodiment, wherein the silver is deposed as a silver layer on a second electrode carrier layer, wherein the second electrode carrier layer comprises a second electrode carrier foil.

Embodiment 31

The method according to the preceding embodiment, wherein the silver is deposed as a silver layer on a polymer foil, in particular sputtered on a polyester foil.

Embodiment 32

The method according to any one of the three preceding embodiments, wherein the test element is produced in a continuous process, typically in a reel-to-reel process.

Embodiment 33

The method according to any one of the four preceding embodiments, wherein the method further comprises cutting the test element into test strips.

Embodiment 34

The method according to any one of the five preceding embodiments, wherein the first electrode, the second electrode and the capillary are formed such that the first electrode and the second electrode are arranged on opposing sides of the capillary.

Embodiment 35

A system for determining at least one property of a sample of a body fluid comprising chloride ions, the system comprising at least one test element according to any one of the preceding embodiments referring to a test element, the system further comprising at least one measurement device configured for performing at least one electrical measurement by using the test element, wherein the measurement device further comprises means for applying a voltage between the first electrode and the second electrode.

In order that the embodiments of the present disclosure may be more readily understood, reference is made to the following examples, which are intended to illustrate but not limit the scope thereof.

FIG. 1A and FIG. 1B show a schematic representation of a typical embodiment of a test element 110 for electrochemically detecting at least one analyte in a sample of a body fluid. Whereas in FIG. 1A the test element 110 is shown during a preparation phase of a method for electrochemically detecting at least one analyte in a sample of a body fluid according to the present disclosure, FIG. 1B schematically depicts the test element 110 during a subsequent detection phase of the indicated method.

In the exemplary embodiment as shown in FIG. 1A and FIG. 1B, the test element 110 is configured in form of a test strip as an electrochemical measuring cell and, thus, comprises a first electrode 112 and a second electrode 114, which are arranged in a face-to-face manner on opposing sides of a test chamber 116 which is, typically arranged in form of a capillary, located between the first electrode 112 and the second electrode 114 in a manner that a surface 118 of the first electrode 112 faces a surface 120 of the second electrode 114. As shown here, the first electrode 112 and the second electrode 114 are, typically, aligned in parallel, in particular as the surfaces 118, 120 which are themselves parallel with respect to each other at least in the direction defined by the length of the test chamber 116.

As shown in FIG. 1A, in the test element as provided according to step a) the surface 118 of the first electrode 112 contacts a test chemistry 122, wherein the test chemistry is a reagent being or comprising a redox mediator M in an oxidized form $M_{ox}$ at the beginning of the preparation phase. Concurrently, the surface 120 of the second electrode 114, being located on the other side of the measuring chamber 116, exhibits silver atoms Ag. For this purpose, the second electrode 114 is typically provided in form of a pure silver coated polymer foil 124, wherein the silver layer, in this particular example, comprises a thickness of 100 nm. The measuring chamber 116 is at least partially filled with blood as a sample 126 of a body fluid such that the sample 126 is capable of getting into contact with the silver atoms Ag located at the surface 120 of the second electrode 114. Herein, the body fluid comprises chloride ions Cl⁻ and, therefore, acts as an electrolyte in the test element 110 being configured as the electrochemical measuring cell. In order to be able to apply a voltage between the first electrode 112 and the second electrode 114, the test element 110 is connected to an electronic circuitry in a separate measurement device (not depicted here).

As further shown in FIG. 1A, a layer of silver chloride AgCl is produced at the silver surface 120 of the second electrode 112 during the preparation phase. For this purpose, the sample 126 of the body fluid is filled during step b) into the test chamber 116, in which the second electrode 114 of the two face-to-face arranged electrodes 112, 114 is a silver electrode whereas the first electrode 112 is at least partially covered with a reagent, which is or comprises the redox mediator in the oxidized form $M_{ox}$. After filling the test chamber 116 during step b) with the sample 126 of the body fluid, the two electrodes 112, 114 are polarized in a manner according to step c). Over a time and with a value that is known for the skilled person to be sufficient for generating the desired layer of silver chloride, a first voltage $V_1$ is applied between the first electrode 112 and the second electrode 114, whereby the second electrode 114 acts as an anode while the first electrode 112 works as a cathode. Consequently, silver ions Ag⁺ are generated from silver atoms Ag located on the surface 120 of the second electrode 114 while the redox mediator located on the surface 118 of the first electrode 112 in the oxidized form $M_{ox}$ is reduced into a reduced form $M_{red}$. Concurrently, the silver ions Ag⁺ generated such on the surface 120 of the second electrode 114 form the compound silver chloride AgCl together with the chloride ions Cl⁻ provided by the sample 126 of the body fluid. The silver chloride AgCl as formed in this manner, thus, precipitates in form of the desired silver chloride AgCl layer on the silver surface 120 of the second electrode 114. Thus, instead of creating the Ag/AgCl electrode during the production process according to the state of the art, the layer of silver chloride AgCl is generated during a regular use of the test element after application of the sample 126 of the body fluid to the test element 110. After the silver chloride AgCl layer has achieved the desired dimensions, the preparation phase may be terminated. Thereafter, the first electrode 112 and the second electrode 114 may, advantageously, be disconnected from the polarization, typically during a stationary phase, which, in this particular example may last for 3 seconds. This period of time may allow the redox mediator being present in the reduced form $M_{red}$ after step c) diffusing away from the surface 118 of the first electrode 120 during the stationary phase.

As shown in FIG. 1B, the subsequent detection phase commences by switching the polarity of the applied voltage. Herein, a second voltage $V_2$ is applied between the first electrode 112 and the second electrode 114, whereby the first electrode 112 now acts as the anode while the second electrode 114 now works as the cathode. Consequently, the redox mediator located on the surface 118 of the first electrode 112 in the reduced form $M_{red}$, which is generated by the analytical detection reaction re-oxidizes at the first electrode 112, which functions here as a working electrode. Thus, it may be possible to determine the concentration of the analyte in the sample 126 of the body fluid, e.g., a glucose Gluc concentration in blood. Herein, usually a test chemistry comprising an enzyme Enz adapted to specifically oxidize the analyte and the redox mediator as electron acceptor and electron shuttle, are used to cover the first electrode 112. In order to provide the electrical current, silver ions $Ag^+$ are reduced to silver atoms Ag at the opposing second electrode 114, which here acts as a counter electrode. Further silver ions $Ag^+$ which may be used for this purpose are provided by a dissociation of the silver chloride AgCl from the layer that was produced during the preceding preparation phase.

Figure 3:
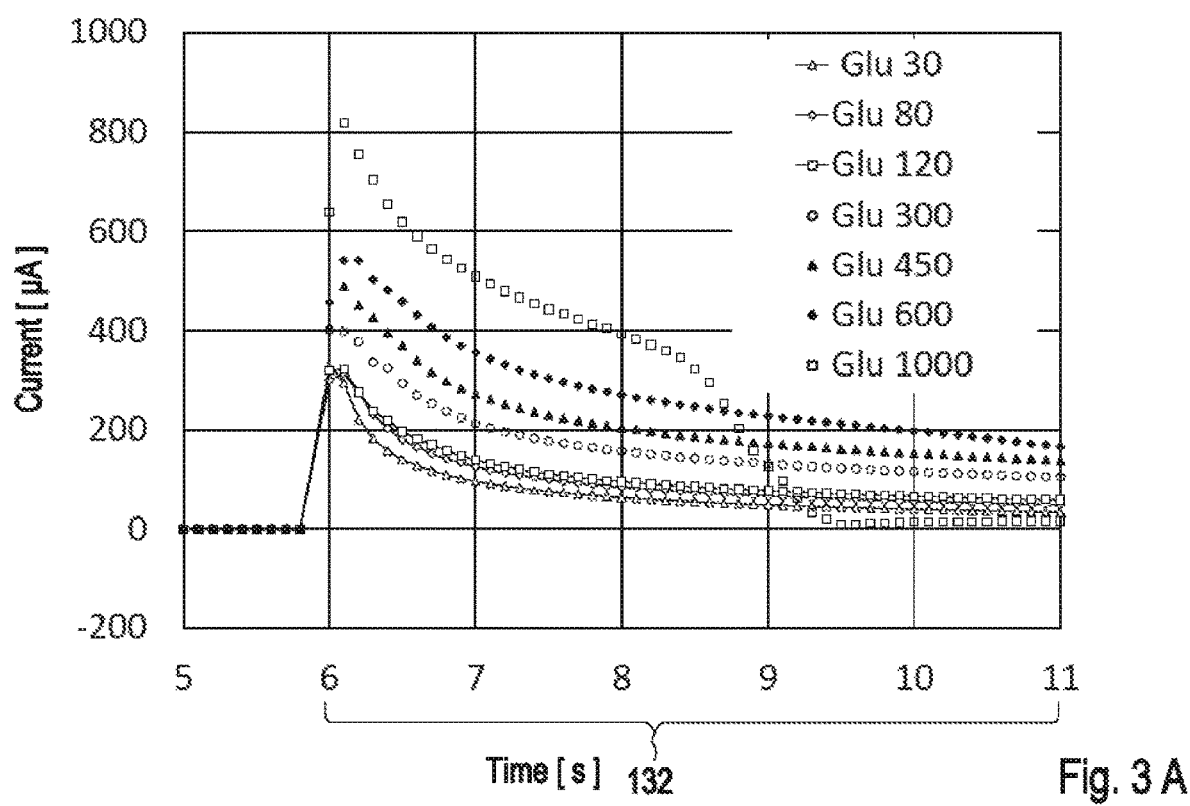
FIG. 3A and FIG. 3B show experimental results for the current response during the detection phase after the preceding preparation phase (FIG. 3A) and—for comparison purposes—after a deliberate omission of the preceding preparation phase (FIG. 3B)
Figure 3:
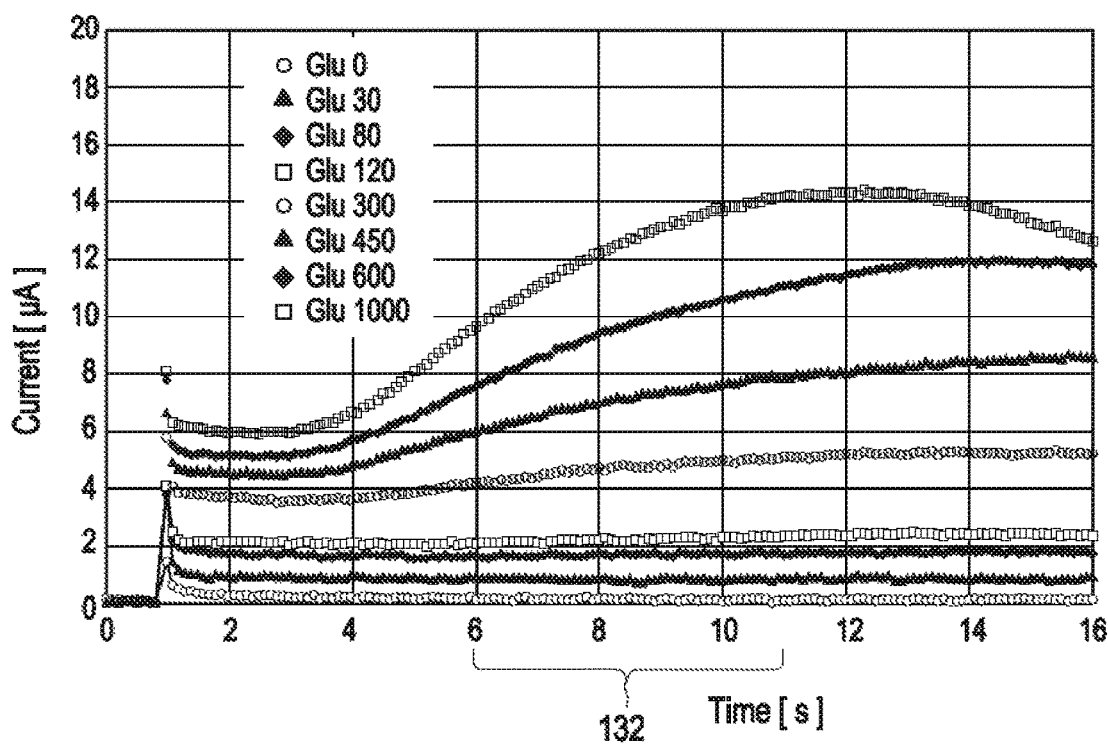
Figure 4:
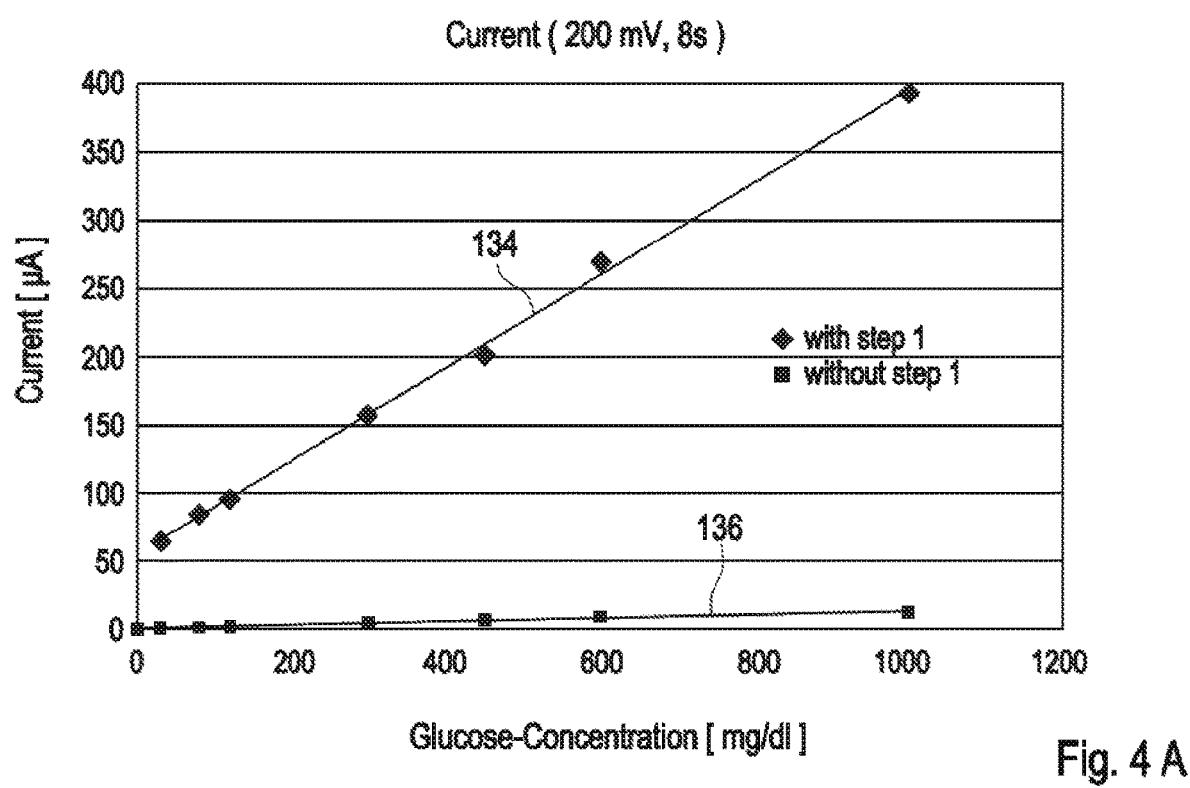
FIG. 4A and FIG. 4B show a representation of the current response values at a definite time (8 s in FIG. 4A and 10 s in FIG. 4B) versus the glucose concentration in a sample.
Figure 4:
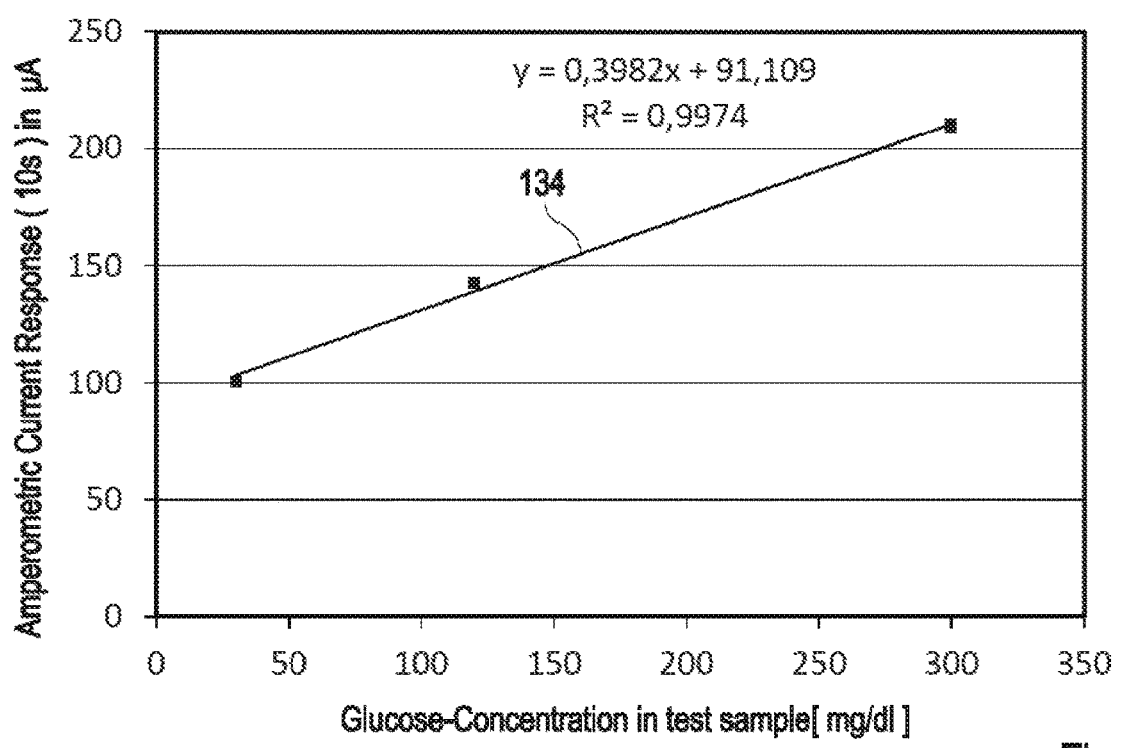

In the following, FIG. 2 to FIG. 4 display experimental results that have been acquired by employing a glucose sensor test strip as the test element 110 according to the present disclosure in a face-to-face configuration. In this particular embodiment, the first electrode 112 comprises a gold sputtered plastic foil while the second electrode 114 comprises a silver sputtered polyester foil. Herein, the first electrode 112 is covered with a dried reagent as the test chemistry, wherein the test chemistry comprises a FAD glucose-dehydrogenase enzyme system and a nitrosoaniline/phenylenediamine redox mediator system.

FIG. 2 shows experimental results of a current response versus time as measured by the measurement device connected to the glucose sensor test strip as described above, which has been employed as the test element 110. Herein, a first step 128 can be attributed to the preparation phase, in which the layer of the silver chloride AgCl is generated at the silver surface 120 of the second electrode 114 by application of the first voltage $V_1$ between the two electrodes 112, 114 with a value of −800 mV, whereby the second electrode 114 acts as an anode while the first electrode 112 works as a cathode. Thereafter, a second step 130 is performed, during which both the first electrode 112 and the second electrode 114 are disconnected from the electrical polarization, so that a zero voltage electrode discharge can be observed. This observation proves that the redox mediator being present in the reduced form $M_{red}$ diffuses away from the surface 118 of the first electrode 120 during the stationary phase. Thereafter, a third step 132 can be attributed to the detection phase, in which the glucose concentration in the blood sample has been determined by using the nitrosoaniline/phenylenediamine redox mediator system at a second voltage $V_2$ of +200 mV applied across the two electrodes 112, 114, whereby the second electrode 114 acts as a cathode while the first electrode 112 works as an anode.

In FIG. 3A, the response current during the third step 132, which is attributed to the detection phase, is displayed for a number of samples comprising different glucose concentrations from 30 mg/dl to 1000 mg/dl. As can be seen for the glucose concentrations in a range from 30 mg/dl to 600 mg/dl, the amperometric current is not limited by the second electrode 114, which acts as the counter electrode. Only with the very high concentration of 1000 mg/dl the amperometric current exhibits a breakdown, thus revealing an exhaustion of the AgCl layer as generated in the preceding preparation phase.

FIG. 3B shows a comparative example, in which the preparation phase has been replaced by an open-circuit phase. Accordingly, no AgCl layer could have been generated during this phase. This assumption is demonstrated by the observation in FIG. 3B that only very low currents, about 50 times lower compared to FIG. 3A, occur. These very low currents are supposed to be generated by a diffusion of reaction products from the first electrode 112 to the opposing second electrode 114.

FIG. 4A and FIG. 4B display two diagrams in which response values at definite times—8 s in FIG. 4A and 10 s in FIG. 4B—are plotted versus the glucose concentration of the blood sample. Herein, the definite times refer to the time that has passed since a detection of the dose. From both figures, a linear response 134 can be derived in a first case in which the preparation phase ("with step 1") has been performed according to the present disclosure. For comparison, a flat response 136 may be observed in a second case in which the preparation phase according to the present disclosure has been omitted ("without step 1").

Herein, the flat response 136 refers to a situation that is similar to what is described in US 2002/112969 A1, EP 1 343 007 A1, or U.S. Pat. No. 6,153,069 A, which, as mentioned above, each disclose a method for a generation of a silver chloride (AgCl) layer. Without application of the first voltage $V_1$ between the first electrode 112 as the cathode and the second electrode 114 as the anode and, thus, in contrast to the present disclosure, only small amounts of silver ions $Ag^+$ may be generated. As can be derived from a comparison between the linear response 134 and the flat response 136 in FIG. 4A, the application of the electrical potential during the preparation phase according to present disclosure allows providing a considerably increased amount of silver ions $Ag^+$, which results in a significant increase of the current response. Thus, the apparent difference between the courses of the linear response 134 and the flat response 136 as illustrated in FIG. 4A clearly demonstrates that only the present disclosure shows the capability of an electrochemical generation of $Ag^+$ ions by applying an electrical potential between the electrodes 112, 114.

In a further embodiment, the method and devices according to the present disclosure may be applied with a modified coagulation test strip based on the COAGUCHEK XS test (Roche Diagnostics). Herein, a special redox mediator forming part of the test chemistry on the first electrode 112 as the working electrode is reduced and the resulting electrical current is measured. This redox mediator is already used here in a so-called "OCB pre-step" for determining whether the test element 110 may still be applicable, in particular since it had been exposed to warm and humid conditions only over a permissible duration. In order to maintain the detection current and in contrast to the COAGUCHEK XS test (Roche Diagnostics), the second electrode 114, which acts as the counter electrode, now comprises a thin silver layer sputtered polymer foil in a face-to-face configuration with the first electrode 112 according to the present disclosure. Thus, the redox mediator on the first electrode 112 may be reduced and, concurrently, the layer of the silver chloride AgCl may be generated by oxidizing the silver on the second electrode 114. Subsequently, a redox tag may be cut off from a peptide substrate by an activated thrombin for measuring a coagulation time, i.e., a pro-thrombin activation time. The redox tag may then be detected by an anodic polarization of the first electrode 112 by applying a suitable second voltage $V_2$ between the two electrodes 112, 114, whereby the redox tag becomes oxidized. In order to support an oxidation process of the redox tag at the first electrode 112, the second electrode 114 may provide a reduction process, by which the silver ions $Ag^+$ may be reduced to silver atoms Ag and the previously produced layer of silver chloride AgCl may dissociate into silver ions $Ag^+$ and chloride ions $Cl^-$.

LIST OF REFERENCE NUMBERS 110 test element
112 first electrode
114 second electrode
116 test chamber
118 surface of the first electrode
120 surface of the second electrode
122 test chemistry
124 silver coated polymer foil
126 sample of the body fluid
128 first step (preparation phase)
130 second step (stationary phase)
132 third step (detection phase)
134 linear response
136 flat response It is noted that terms like "preferably," "commonly" and typically are not utilized herein to limit the scope of the claimed subject matter or to imply that certain features are critical, essential, or even important to the structure or function of the embodiments disclosed herein. Rather, these terms are merely intended to highlight alternative or additional features that may or may not be utilized in a particular embodiment of the present disclosure.

For purposes of describing and defining the subject matter of the present disclosure it is noted that the terms "substantially" and "about" may be utilized herein to represent the inherent degree of uncertainly that may be attributed to any quantitative comparison, value, measurement, or other representation. These terms are also utilized herein to represent the degree by which a quantitative representation may vary from a stated reference without resulting in a change in the basic function of the subject matter at issue.

It will be apparent to those skilled in the art that various modifications and variations can be made to the embodiments described herein without departing from the spirit and scope of the claimed subject matter. Thus, it is intended that the specification cover the modifications and variations of the various embodiments described herein, provided such modifications and variations come within the scope of the appended claims and their equivalents.

What is claimed is:

1. A method for electrochemically detecting at least one analyte in a sample of a body fluid comprising chloride ions, the method comprising the steps:
    a) providing at least one test element, wherein the test element comprises at least one first electrode contacting a test chemistry and at least one second electrode, wherein the test chemistry is or comprises a redox mediator in an oxidized form, wherein, in an absence of the sample, a surface of the second electrode adapted to contact the sample of the body fluid consists of silver metal;
    b) contacting both the first electrode and the second electrode with the sample of the body fluid comprising the chloride ions;
    c) applying a first voltage ($V_1$) between the first electrode as a cathode and the second electrode as an anode for a time and with a voltage sufficient for forming a layer of silver chloride at the surface of the second electrode, wherein the oxidized form of the redox mediator is transformed into a reduced form;
    d) applying a second voltage ($V_2$) between the first electrode as the anode and the second electrode as the cathode, wherein
        applying the first voltage ($V_1$) is terminated after step c) and a period of time passes before the second voltage ($V_2$) is applied according to step d); and
    e) determining an electrical signal between the first electrode and the second electrode, whereby the analyte in the sample of the body fluid comprising the chloride ions is detected, wherein detecting the analyte comprises re-oxidizing the redox mediator.

2. The method of claim 1, wherein a measurement device adapted to interact with the test element is used to apply the first voltage ($V_1$) and/or the second voltage ($V_2$) between the first electrode and the second electrode.

3. The method of claim 1, wherein the time during which the first voltage ($V_1$) is applied between the first electrode as the cathode and the second electrode as the anode during step c) is at least 0.2 s.

4. The method of claim 1, wherein the second electrode comprises a silver layer being disposed on a second electrode carrier layer, wherein the second electrode carrier layer comprises a second electrode carrier foil, wherein the silver layer comprises of a thickness in a range from 10 nm to 1000 nm.

5. The method of claim 1, wherein the sample of the body fluid comprises blood, plasma, serum, urine, saliva, or an interstitial fluid.

6. The method of claim 5, wherein the sample of the body fluid comprises whole blood.

7. The method of claim 1, wherein the period of time that passes before the second voltage ($V_2$) is applied according to step d) is between about 0.5 seconds and about 30 seconds.

8. The method of claim 1, wherein the period of time that passes before the second voltage ($V_2$) is applied according to step d) is between about 3 seconds and about 10 seconds.

9. A system for determining at least one property of a sample of a body fluid comprising chloride ions, the system comprising at least one test element for electrochemically detecting at least one analyte in a sample of a body fluid comprising chloride ions, wherein the test element comprises at least one first electrode contacting a test chemistry, wherein the test chemistry is or comprises a redox mediator in an oxidized form, and at least one second electrode, wherein, in an absence of the sample, a surface of the second electrode adapted to contact the sample consists of silver metal, the system further comprising at least one measurement device configured for performing at least one electrical measurement by using the test element, wherein the measurement device applies a first voltage ($V_1$) between the first electrode as a cathode and the second electrode as an anode for a time and with a voltage sufficient for forming a layer of silver chloride at the surface of the second electrode, wherein the oxidized form of the redox mediator is transformed into a reduced form, and wherein the measurement device applies a second voltage ($V_2$) between the first electrode as the anode and the second electrode as the cathode, wherein applying the first voltage ($V_1$) is terminated and a period of time passes before the second voltage ($V_2$) is applied.

10. The system of claim 9, wherein the second electrode comprises a silver layer being disposed on a second electrode carrier layer, wherein the second electrode carrier layer comprises a second electrode carrier foil, wherein the silver layer comprises of a thickness in a range from 10 nm to 1000 nm.

11. The system of claim 9, further comprising at least one capillary adapted to receive the sample, wherein the first electrode and the second electrode are arranged on opposing sides of the capillary.

12. The system of claim 9, wherein the period of time that passes before the second voltage ($V_2$) is applied is between about 0.5 seconds and about 30 seconds.

13. The system of claim 9, wherein the period of time that passes before the second voltage ($V_2$) is applied is between about 3 seconds and about 10 seconds.

* * * * *